(12) United States Patent
Shu et al.

(10) Patent No.: US 9,557,282 B1
(45) Date of Patent: Jan. 31, 2017

(54) HIGH PRECISION DETECTOR ROBOT ARM SYSTEM

(71) Applicants: Deming Shu, Darien, IL (US); Yong Chu, Northport, NY (US)

(72) Inventors: Deming Shu, Darien, IL (US); Yong Chu, Northport, NY (US)

(73) Assignee: U.S. Department of Energy, Washington, DC (US)

( * ) Notice: Subject to any disclaimer, the term of this patent is extended or adjusted under 35 U.S.C. 154(b) by 268 days.

(21) Appl. No.: 14/303,149

(22) Filed: Jun. 12, 2014

Related U.S. Application Data (60) Provisional application No. 61/835,700, filed on Jun. 17, 2013.

(51) Int. Cl.
*H01J 31/49* (2006.01)
*G01N 23/20* (2006.01)
*G21K 7/00* (2006.01)

(52) U.S. Cl.
CPC ........ *G01N 23/20008* (2013.01); *G01N 23/20* (2013.01); *G21K 7/00* (2013.01); *Y10S 901/41* (2013.01)

(58) Field of Classification Search
CPC .... G01N 23/2008; G01N 23/20; G01N 23/04; Y10S 901/41
USPC .......................................... 378/189, 204, 205
See application file for complete search history.

(56) References Cited

U.S. PATENT DOCUMENTS 7,331,714 B2    2/2008   Shu et al.
2010/0232574 A1*   9/2010   Ahn ...................... A61B 6/447
                                                                                   378/167

* cited by examiner

*Primary Examiner* — Courtney Thomas
(74) *Attorney, Agent, or Firm* — Timothy L. Harney; Daniel D. Park; Brian J. Lally (57) ABSTRACT

A method and high precision robot arm system are provided, for example, for X-ray nanodiffraction with an X-ray nanoprobe. The robot arm system includes duo-vertical-stages and a kinematic linkage system. A two-dimensional (2D) vertical plane ultra-precision robot arm supporting an X-ray detector provides positioning and manipulating of the X-ray detector. A vertical support for the 2D vertical plane robot arm includes spaced apart rails respectively engaging a first bearing structure and a second bearing structure carried by the 2D vertical plane robot arm.

17 Claims, 9 Drawing Sheets

HIGH PRECISION DETECTOR ROBOT ARM SYSTEM

RELATED APPLICATIONS

The present application is a utility application claiming the benefit of provisional application U.S. Pat. Appln. No. 61/835,700, filed on Jun. 17, 2013 by the same inventors, the entirety of which is hereby incorporated by reference.

GOVERNMENT INTERESTS

The United States Government has rights in this invention pursuant to Contract No. DE-AC02-06CH11357 between the United States Government and UChicago Argonne, LLC representing Argonne National Laboratory.

FIELD OF INVENTION

The present invention relates generally to precision positioning stage systems, and more particularly, relates to a method and high precision robot arm system.

DESCRIPTION OF THE RELATED ART

A traditional way to perform diffraction measurement is to use a diffractometer. In carrying out diffraction measurement using a small focused beam, or so-called nanodiffraction, using a conventional diffractometer faces three major instrument challenges. First, rotation motion of the sample typically has a large (>10 microns) run-out error known as a sphere of confusion. Second, the circles for the detector are mechanically coupled to the sample, causing unwanted displacement of the sample position when the detector is rotated. Third, some X-ray microscopes used for micro or nanodiffraction use a large vacuum enclosure, making it virtually impossible to use a conventional diffractometer.

U.S. Pat. No. 7,331,714 by Deming Shu, Jorg M. Maser, Barry Lai, Stefan Vogt, Martin V. Holt, Curt A. Preissner, Robert P. Winarski, and Gregory B. Stephenson, entitled Optomechanical Structure for a Multifunctional Hard X-Ray Nanoprobe Instrument discloses a multifunctional hard X-ray nanoprobe instrument for characterization of nanoscale materials and devices includes a scanning probe mode with a full field transmission mode. The scanning probe mode provides fluorescence spectroscopy and diffraction contrast imaging. The full field transmission mode allows two-dimensional (2-D) imaging and tomography. The nanoprobe instrument includes zone plate optics for focusing and imaging. The nanoprobe instrument includes a stage group for positioning the zone plate optics. The nanoprobe instrument includes a specimen stage group for positioning the specimen. An enhanced laser Doppler displacement meter (LDDM) system provides two-dimensional differential displacement measurement in a range of nanometer resolution between the zone-plate optics and the sample holder. A digital signal processor (DSP) implements a real-time closed-loop feedback technique for providing differential vibration control between the zone-plate optics and the sample holder.

There are many synchrotron radiation instrument applications that require a very high reproducibility for multidimensional linear positioning systems, for example, with nanometer resolution. For X-ray microdiffraction and nanodiffraction studies precision is a key to success. More precise probes and robotic arms are needed to get better results. Thus, it is desirable to provide a method and high precision robot arm system suitable for X-ray nanodiffraction with X-ray nanoprobe.

These and other objects, aspects, and advantages of the present disclosure will become better understood with reference to the accompanying description and claims.

SUMMARY

In brief, a method and high precision robot arm system are provided, for example, for X-ray nanodiffraction with an X-ray nanoprobe. The robot arm includes duo-vertical-stages and a kinematic linkage system. A two-dimensional (2D) vertical plane ultra-precision robot arm supporting an X-ray detector provides positioning and manipulating of the X-ray detector. A vertical support for the 2D vertical plane robot arm includes spaced apart rails respectively engaging a first bearing structure and a second bearing structure carried by the 2D vertical plane robot arm.

In accordance with features of the invention, the robot arm system includes a granite base with an air-bearing support, a 2D horizontal base stage, and a vertical axis goniometer with the 2D vertical plane robot arm. In accordance with features of the invention, the robot arm system includes a 3D fast scanning stages group provided with the robot arm. In accordance with features of the invention, the X-ray detector provided with the robot arm includes a 2D X-ray pixel detector. In accordance with features of the invention, the high-precision robot arm system enables effective positioning and manipulating of an x-ray detector for an X-ray nanodiffraction experimental station at a hard X-ray nanoprobe (HXN) beamline. In accordance with features of the invention, the robot arm system includes duo-vertical-stages and a kinematic linkage system providing high load capacity with micron level positioning repeatability.

DETAILED DESCRIPTION

The following description is provided to enable any person skilled in the an to use the invention and sets forth the best mode contemplated by the inventor for carrying out the invention. Various modifications, however, will remain readily apparent to those skilled in the art, since the principles of the present invention are defined herein specifically to provide a method and high precision robot arm system are provided, for example, for X-ray nanodiffraction with an X-ray nanoprobe.

For the X-ray microscope for the Hard X-ray nanoprobe (HXN) Beamline at the National Synchrotron Light Source II (NSLS-II) of Brookhaven National Laboratory, which is designed for X-ray microscopy capabilities with an initial spatial resolution of 10 nm, a novel design approach now is taken for nanodiffraction. In the new design, the detector positioning system is completely de-coupled from the sample stage stack together with the use of a high-precision robot arm system in generating full spherical coordinate motions for an array detector. These motion degrees of freedom include the horizontal diffraction angle, the vertical diffraction angle, and the sample-to-detector distance, called detector distance in the following description. When performing Bragg crystallography, adjusting detector distance is important because it defines the maximum range of diffraction angle, which contributes to the special resolution limit of the reconstruction.

For example, the instrument requirement for the NSLS-II HXN beamline is to achieve a horizontal diffraction angular range from −5 to 45°, and the sample-to-detector distance from 0.25 to 0.54 m (0.25 to 1.5 m with base station positioning). The horizontal diffraction angle is produced by using a 2-D horizontal base stage plus an in-plane goniometer. The vertical diffraction angle is achieved using a vertical plane robot arm structure of the invention. In addition, a 3-D fast scanning stages group of the invention is used to generate the detector distance plus the capability to raster the area detector, in order to achieve a larger q-range.

Figure 1:
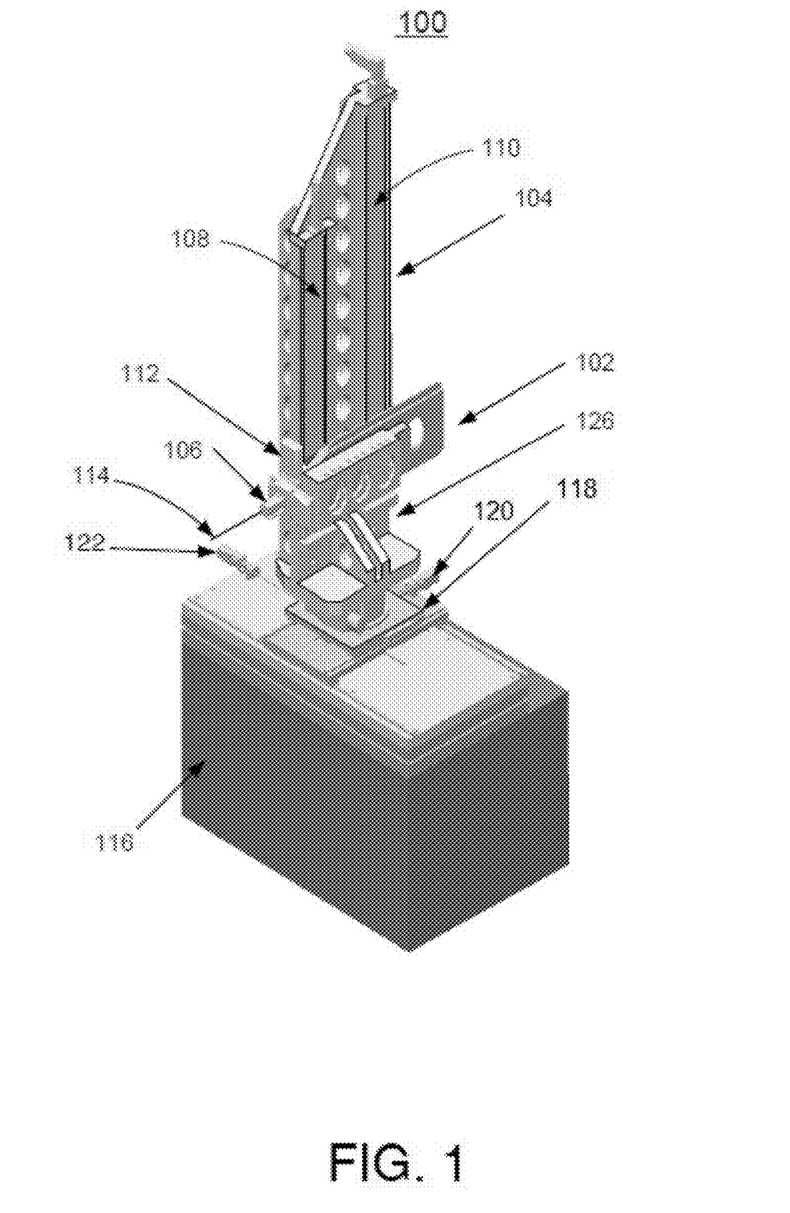
FIG. 1 schematically illustrates not to scale an example high precision robot arm system for X-ray nanodiffraction in accordance with a preferred embodiment.

Having reference now to the drawings, in FIG. 1, there is shown an example high precision robot arm system for X-ray nanodiffraction generally designated by the reference character 100 including an example robot arm generally designated by the reference character 102 together with a robot arm vertical support generally designated by the reference character 104 in accordance with the preferred embodiment.

In accordance with features of the invention, the 2D vertical plane robot arm 102 with duo-vertical-stages and a kinematic linkage system provide high load capacity with micron level positioning repeatability. For example, the 2D vertical plane robot arm 102 is 10-20-times better than typical Cartesian robot arm and joints robot arm with similar load capacity.

The high precision robot arm system 100 includes the two-dimensional (2D) vertical plane ultra-precision robot arm 102 supporting an X-ray detector 106 to provide positioning and manipulating of the X-ray detector. The X-ray detector 106, for example includes a 2D X-ray pixel detector.

While the high precision robot arm system 100 is described particularly for use for X-ray nanodiffraction with an X-ray nanoprobe, it should be understood that the mechanical design may be applied in other fields of precision positioning devices. Other fields of precision positioning devices potentially include additive manufacturing devices (3D printing and sputtering deposition), laser applications, microsurgery, and precision assembly.

Figure 2:
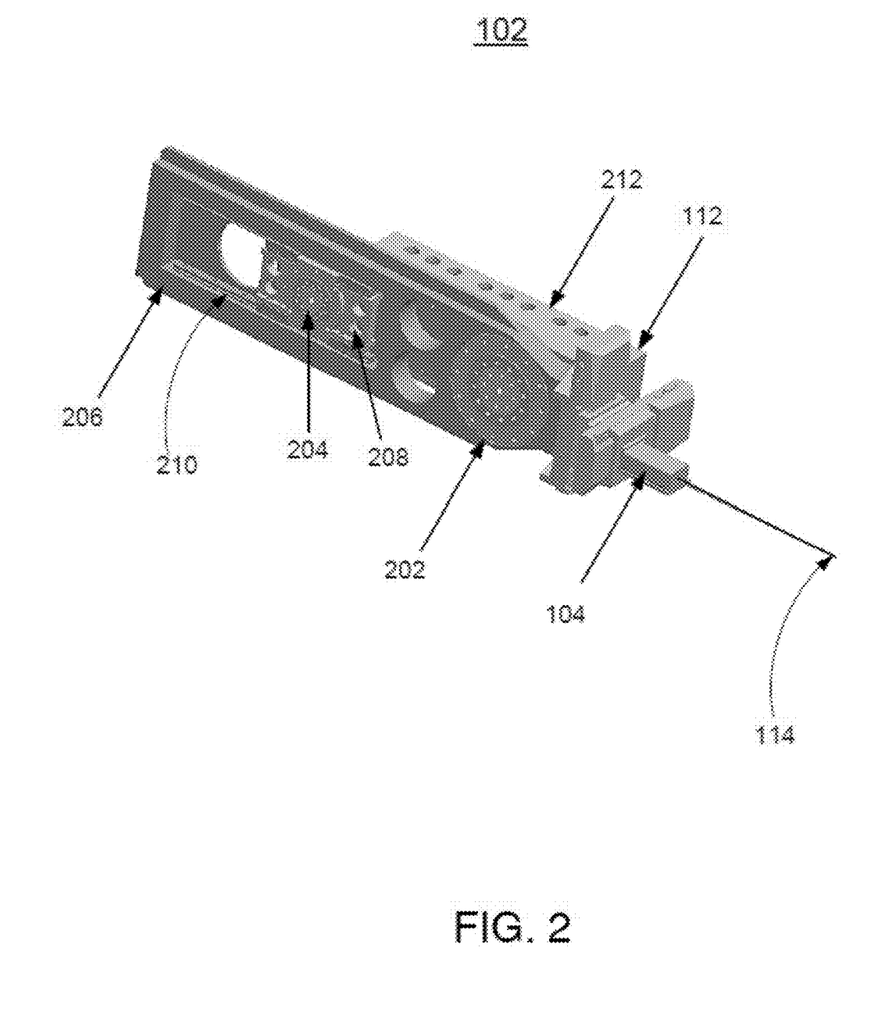
FIG. 2 schematically illustrates not to scale the robot arm linkage sub-assembly.
Figure 3:
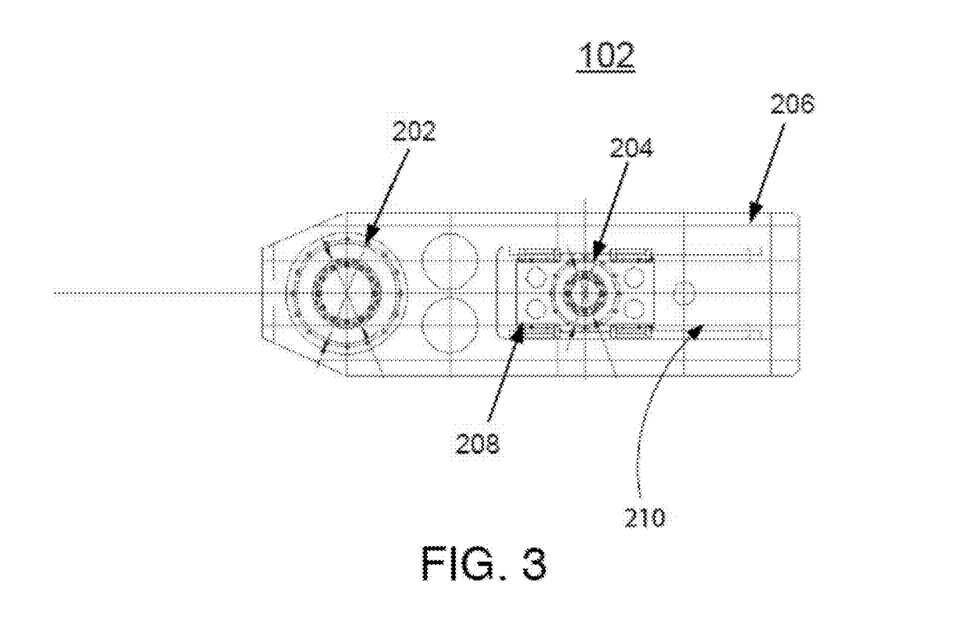
FIG. 3 schematically illustrates not to scale the robot arm linkage sub-assembly.

The vertical support 104 for the 2D vertical plane robot arm 102 includes a pair of spaced apart rails 108, 110 respectively engaging a first bearing structure 202 and a second bearing structure 204 carried by the 2D vertical plane robot arm 102, as shown in FIG. 2.

The robot arm system 100 includes a 3D fast scanning stages group generally designated by the reference character 112 provided together with the 2D vertical plane robot arm 102. The 2D vertical plane robot arm 102 carries a robot finger or pin 114 for supporting a sample, for example at an industrial application.

Figure 8:
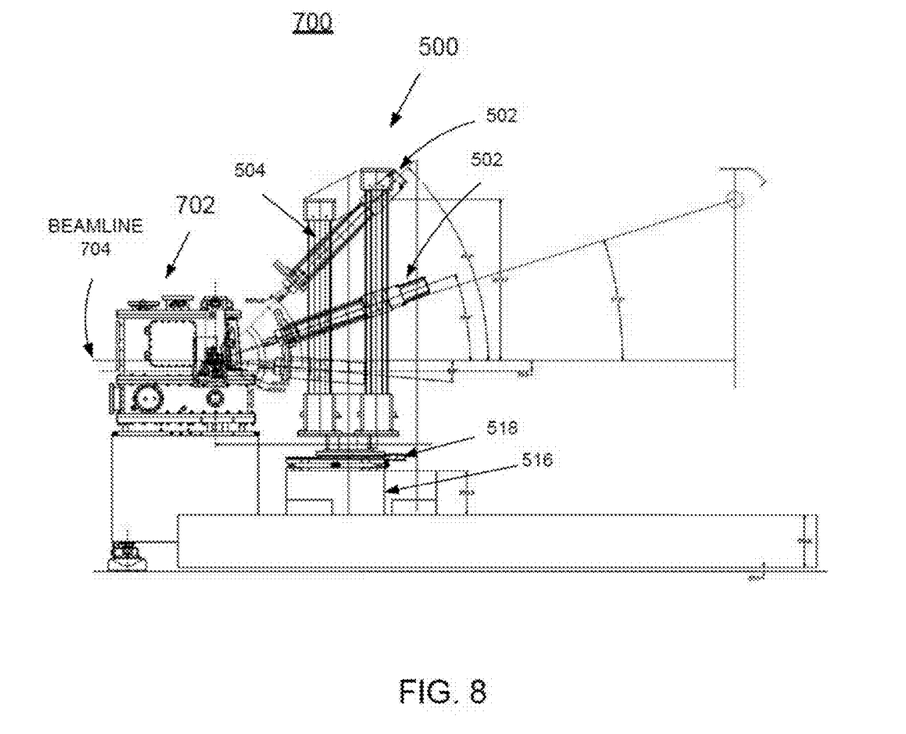
FIG. 8 schematically illustrates not to scale top view of the exemplary high precision robot arm system together with an X-ray nanodiffraction unit in accordance with a preferred embodiment.
Figure 9:
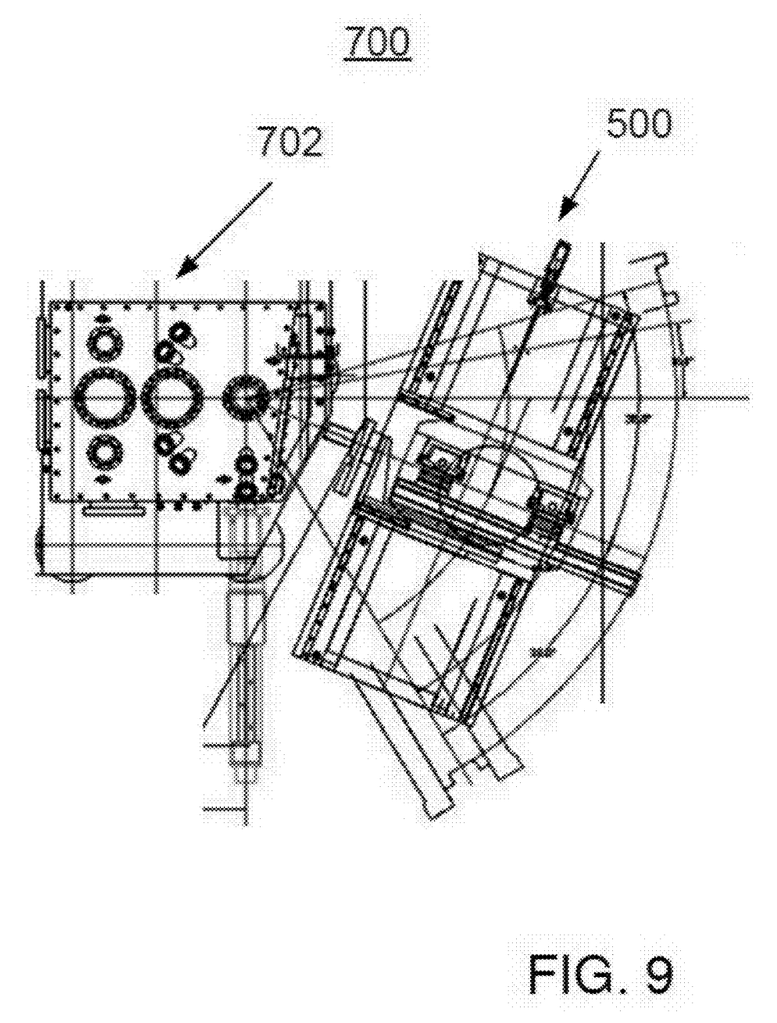
FIG. 9 schematically illustrates not to scale side view of the exemplary high precision robot arm system together with an X-ray nanodiffraction unit in accordance with a preferred embodiment.

In accordance with features of the invention, the high-precision robot arm system enables effective positioning and manipulating of the X-ray detector 106 for an X-ray nanoprobe experimental station at a hard X-ray nanoprobe (HXN) beamline, such as an X-ray nanodiffraction unit 702 as illustrated and described with respect to FIGS. 8 and 9.

The robot arm system 100 includes a granite base with an air-bearing support 116, a 2D horizontal base stage 118 including fine positioning adjusters 120, 222. The robot arm system 100 includes a vertical axis goniometer 126 carrying the 2D vertical plane robot arm support 104.

The normal load capacity of an example robot arm 102 is 60 kg, which is not only capable to cover the total weight of an array detector 106, such as a Timepix™ QTPX-262K (Amsterdam Scientific Instruments B.V.), and the 3D fast scanning stages group 112 including a pair of motorized stages for the area detector raster scan, but also is capable to carry out the dynamic forces generated during the detector raster scan. The load capacity also provides for positioning loads such as lasers and additive manufacturing devices.

Referring also to FIGS. 2, 3, 4, and 5, the detector robot arm 102 is shown. The first bearing structure 202 and second bearing structure 204 carried by the 2D vertical plane robot arm 102 are assembled with a frame member 206 of the robot arm 102. The second bearing structure 204 includes a support member 208 received within a cavity rail or slot 210 formed in the frame member 206. The frame member 206 of the robot arm 102 includes a separate linkage or frame member 212 provided with the 3D fast scanning stages group 112.

FIG. 2 shows the robot arm linkage sub-assembly 102. The sub-assembly 102 consists of the frame member 206 providing a linkage base 206, cavity rail or slot 210 forming a high rigidity linear rolling guide 210, and the pair of high rigidity cross-roller bearings 202, 204. The first bearing structure 202 is mounted on the linkage base 206, and the section bearing structure 204 is mounted on the carriage 208 of the rolling guide 210. The linkage sub-assembly 102 is connected to the carriages 108, 110 of FIG. 1, (and 508, 510 of FIG. 6) of the two vertical linear stages through the pair of cross-roller bearings 202, 204. The vertical plane robot arm 102 is positioned in the vertical plane by the two vertical linear stages kinematically. A set of motorized 3-D fast scanning stages group 112 is mounted onto the linkage base to perform the detector raster scan and adjust the detector distance for the 2-D area detector 106. Table 3 summarized the example design specifications of the robot arm vertical linear stages.

Figure 4:
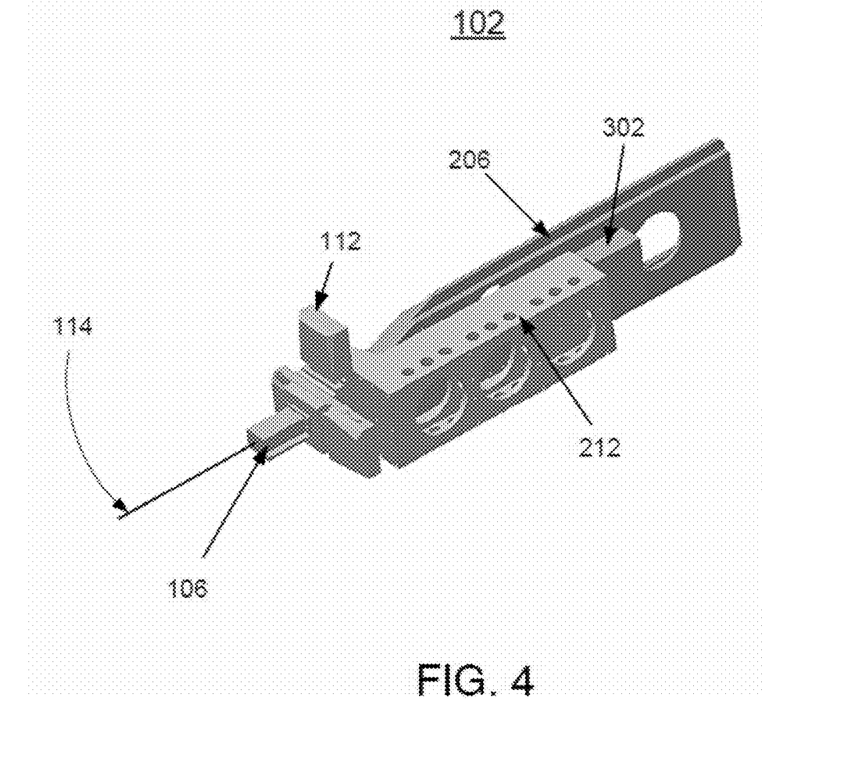
FIG. 4 schematically illustrates not to scale the robot arm linkage sub-assembly.
Figure 5:
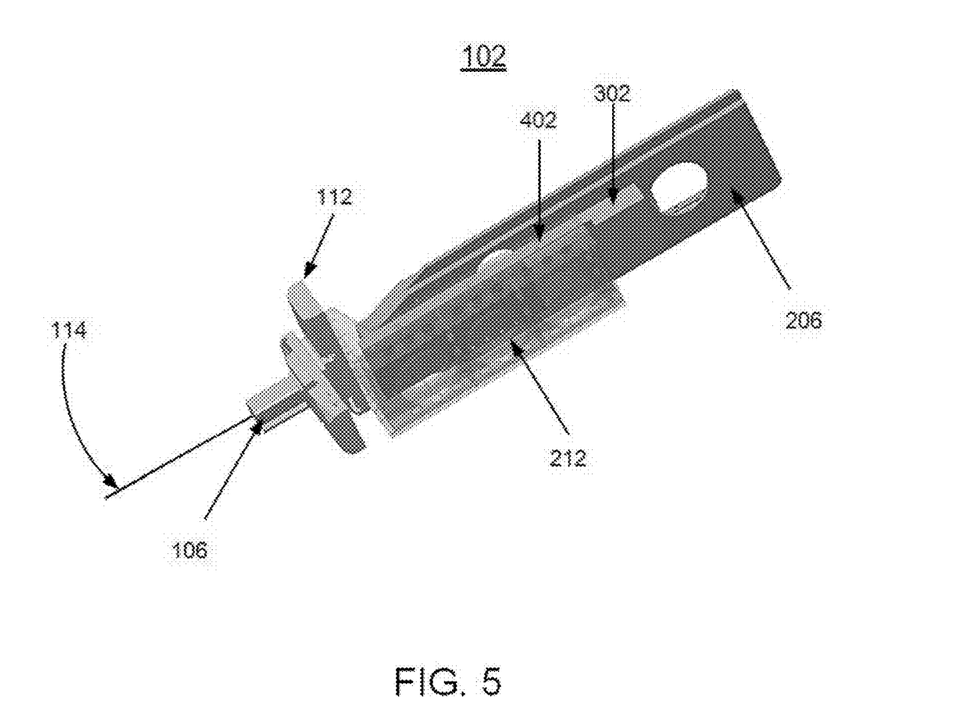
FIG. 5 schematically illustrates not to scale the robot arm linkage sub-assembly.

The linkage or frame member 212 is shown in FIG. 4 is slidingly mounted on a stage base 302. The frame member 212 is shown transparently in FIG. 5 to illustrate the frame member 212 mounted on a carriage 402 after the stage base 302 carrying the frame member 212.

In accordance with features of the invention, the detector robot arm 102 is rotatable and slidingly moved along the vertical support member 110 for positioning and manipulating of the X-ray detector 106.

Referring also to FIGS. 6, 7, 8, and 9, there is shown another exemplary high precision robot arm system for X-ray nanodiffraction generally designated by the reference character 500 including an example detector robot arm generally designated by the reference character 502 together with a robot arm vertical support generally designated by the reference character 504 in accordance with the preferred embodiment. The high precision robot arm system 500 and the detector robot arm 502 provide similar function and operation as the high precision robot arm system 100 and the detector robot arm 102.

Figure 6:
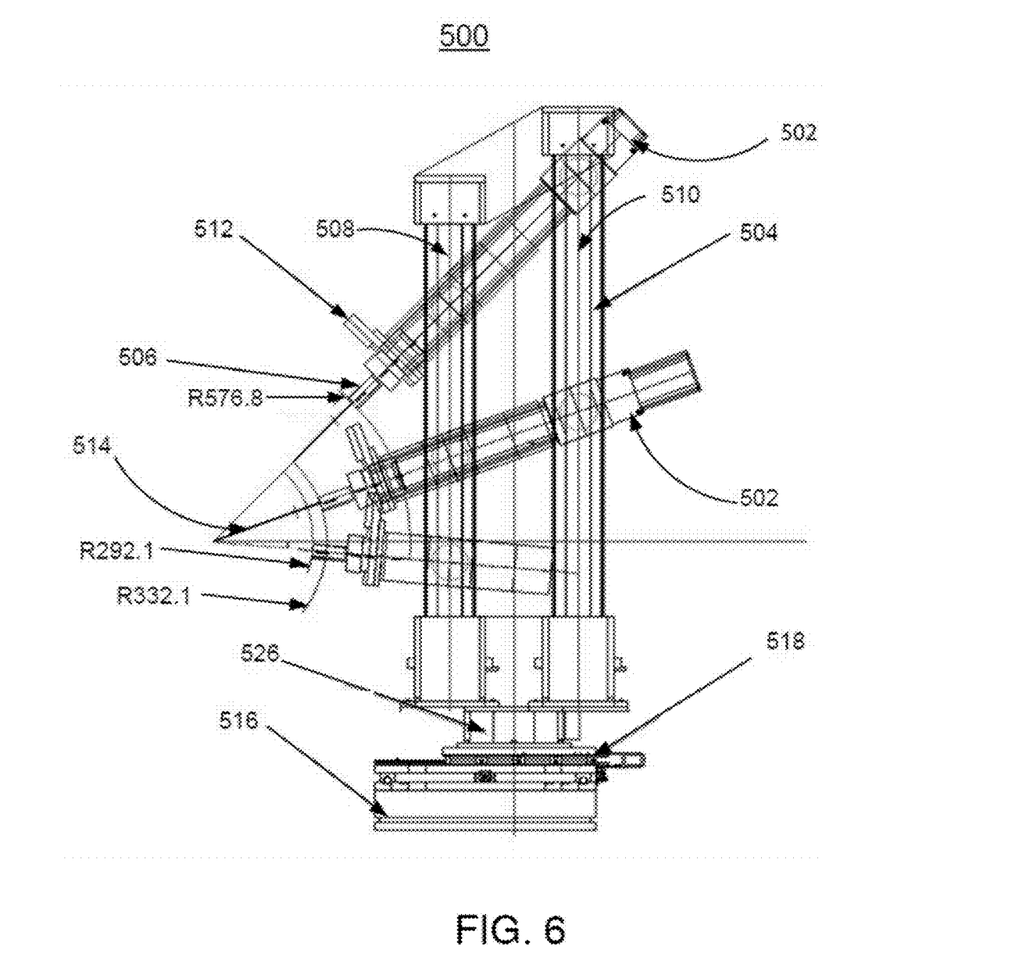
FIG. 6 schematically illustrates not to scale side view of an exemplary high precision robot arm system for X-ray nanodiffraction in accordance with a preferred embodiment.
Figure 7:
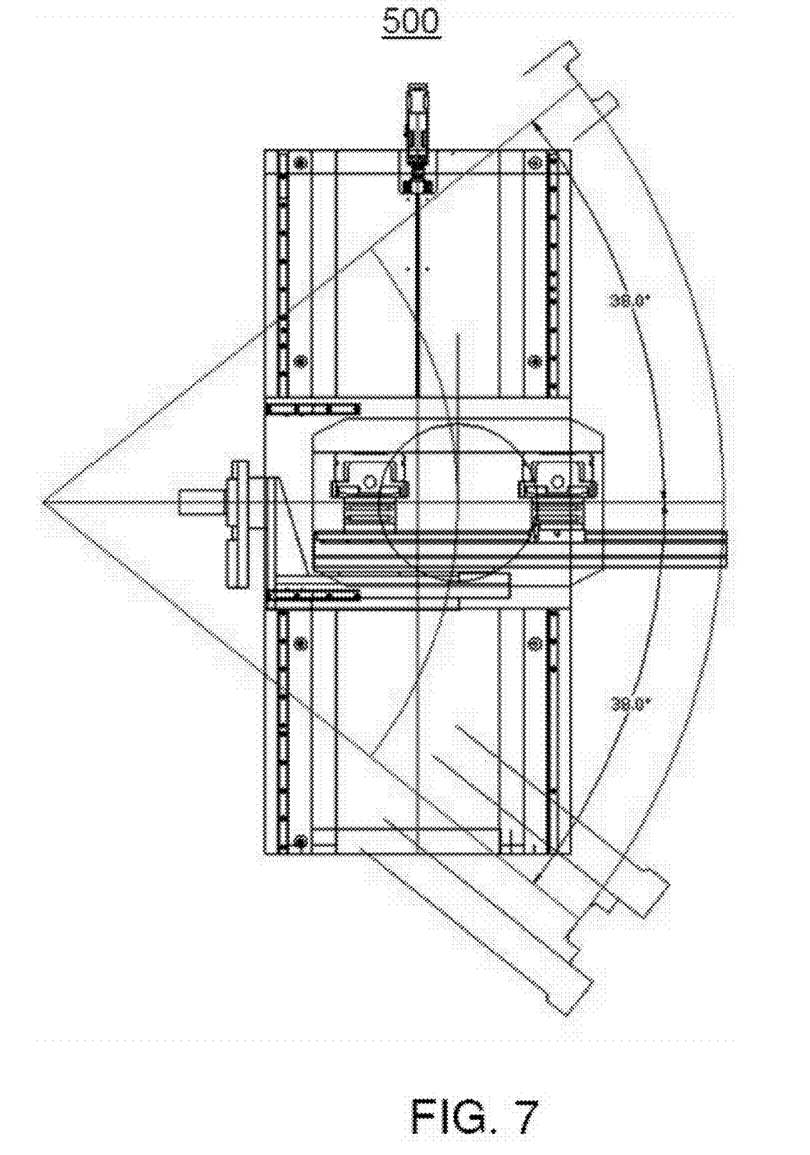
FIG. 7 schematically illustrates not to scale top view of an exemplary high precision robot arm system for X-ray nanodiffraction in accordance with a preferred embodiment.

In FIG. 6, a side view is shown of the high precision robot arm system 500 including the detector robot arm 502 together with the robot arm vertical support 504 with a top view of the high precision robot arm system 500 shown in FIG. 7. The high precision robot arm system 500 includes the two-dimensional (2D) vertical plane ultra-precision robot arm 502 supporting an X-ray detector 506 to provide positioning and manipulating of the X-ray detector. The robot arm system 500 includes a 3D fast scanning stages group generally designated by the reference character 512 provided together with the 2D vertical plane robot arm 502. The 2D vertical plane robot arm 502 carries a robot finger or pin 514 for supporting a sample, for example at an industrial application. The robot arm system 500 includes a granite base with an air-bearing support 516, a 2D horizontal base stage 518 and a vertical axis goniometer 526 carrying the 2D vertical plane robot arm support 504.

In FIGS. 6 and 7, the detector robot arm 502 is illustrated at different positions moved along the vertical support 504 in the operation of the high precision robot arm system 500.

FIGS. 8 and 9 schematically illustrates not to scale side and top views an X-ray nanodiffraction apparatus generally designated by the reference character 700 including the exemplary high precision robot arm system 500 together with an X-ray nanodiffraction unit 702 in accordance with a preferred embodiment. In FIGS. 6 and 7, the detector robot arm 502 is illustrated at different positions moved along the vertical support 504 in the operation of the high precision robot arm system 500.

The initial design goal for the robot arm unidirectional positioning, for example, robot arm 102, 502 repeatability is 20 micron in the experimental station with +/−0.1 degree temperature control. With a better environmental temperature control, +/−0.1 degree temperature control. With a better environmental temperature control positioning repeatability in a few-micron-level should be achievable for the robot arm system 100, 500. This is valuable for the future detector upgrade with high-spatial-resolution pixel sizes.

Table 1 summarizes example main design specifications of the example robot arm systems 100, 500.

TABLE 1

Example main design specifications for the robot arm systems 100, 500.

| Parameter | Value | Units |
| --- | --- | --- |
| Overall dimension | 1700(W) × 2020(L) × 2750(H) | mm |
| Horizontal diffraction angular range | −5−+65 | deg |
| Vertical diffraction angular range | −5−+45 | deg |
| Sample-to-detector distance | 0.25-0.54 | m |
| Sample-to-detector distance (with base positioning) | 0.25-2.5 | m |
| Normal load capacity | 18 | kg |
| Robot base relocation range | 2.5 × 3 | km |
| Unidirectional positioning repeatability | <20 | micron |

Table 2 summarizes example main design specifications of the 2-D horizontal base stage for the robot arm systems 100, 500.

TABLE 2

Example design specifications for robot arm 2-D horizontal base stages 118, 518

| Parameter | Value | Units |
| --- | --- | --- |
| Overall dimension | 1700(W) × 2020(L) × 2750(H) | mm |
| Normal Load Capacity | 500 | kg |
| Stage driver type | Stepping motor with planetary gearhead | |
| Encoder type | Linear grating encoder | |
| Travel range (mm) | 1050(W) × 300(L) | mm Min. |
| incremental motion (micron) | 0.25-1.5 | micron |
| Unidirectional repeatability (micron) | +/−5 | micron |
| Max. speed (mm/sec) | 600 | mm/min |

Each robot arm system 100, 500 has a unique vertical plane robot arm structure. As shown FIGS. 1 and 2, and in FIG. 6, the vertical plane robot arm structure 104, 504 includes a vertical base 104, 504, two THK™ custom-built vertical linear stages 108, 110; 508, 510 or other commercial stages and a robot arm linkage 102, 502, and a 3-D fast scanning stages group 112, 512 to generate the detector distance plus the capability to raster the area detector 106.

TABLE 3

Example design specifications for robot arm vertical linear stages

| Parameter | Value | Units |
| --- | --- | --- |
| Overall Dimension (Upstream stage) | 1520(H) × 200(W) × 58(D) | mm |
| Overall Dimension (Downstream stage) | 1788(H) × 200(W) × 58(D) | mm |
| Travel range (Upstream stage) | 850 | mm |
| Travel range (Downstream stage) | 1210 | mm |
| Vertical Load Capacity | 60 | kg |
| Stage driver type | Stepping motor with planetary gearhead | |
| Encoder type | Linear grating encoder | |
| Min. incremental linear motion | 0.8/full-step 0.02/micro-step | micron |
| Min. incremental angular motion | 2.1/full-step 0.05/micro-step | micro-rad |
| Unidirectional repeatability | +/−3 | micron |
| Max. speed | 160 | mm/min |

In a brief summary, the above describes optomechanical design and example specifications of a high-precision robot arm system 100, 500 to be constructed for the X-ray nano-diffraction experimental station at the HXN beamline for the NSLS-II project. It is expected that its unique vertical plane robot arm structure providing high-precision angular positioning capability for the X-ray nano-diffraction applications with x-ray nanoprobe, will be adopted and used for other X-ray microprobes and nanoprobes to enable high-precision X-ray diffraction capability.

It is to be understood that the above-described arrangements are only illustrative of the application of the principles of the present invention and it is not intended to be exhaustive or limit the invention to the precise form disclosed. Numerous modifications and alternative arrangements may be devised by those skilled in the art in light of the above teachings without departing from the spirit and scope of the present invention. It is intended that the scope of the invention be defined by the claims appended hereto.

In addition, the previously described versions of the present invention have many advantages, including but not limited to those described above. However, the invention does not require that all advantages and aspects be incorporated into every embodiment of the present invention.

All publications and patent documents cited in this application are incorporated by reference in their entirety for all purposes to the same extent as if each individual publication or patent document were so individually denoted.

We claim:
1. A precision robot arm system comprising:
    a two-dimensional (2D) vertical plane robot arm including duo-vertical-stages and a kinematic linkage system supporting an X-ray detector for positioning and manipulating of the X-ray detector and including;
    a first cross-roller bearing structure and a second cross-roller bearing structure carried by said 2D vertical plane robot arm; and
    a vertical support carrying said 2D vertical plane robot arm, said vertical support including spaced apart rails respectively engaging said first cross-roller bearing structure and said second cross-roller bearing structure carried by the 2D vertical plane robot arm, such that said 2D vertical plane robot arm is rotatable and slidingly moved along said vertical support.

2. The precision robot arm system as recited in claim 1 wherein said X-ray detector supported by said 2D vertical plane robot arm includes a 2D X-ray pixel detector.

3. The precision robot arm system as recited in claim 1 includes a granite base with an air-bearing support supporting said vertical support carrying said 2D vertical plane robot arm.

4. The precision robot arm system as recited in claim 1 includes a 2D horizontal base stage mounted on a granite base with an air-bearing support supporting said vertical support carrying said 2D vertical plane robot arm.

5. The precision robot arm system as recited in claim 1 includes a vertical axis goniometer supporting said vertical support carrying said 2D vertical plane robot arm.

6. The precision robot arm system as recited in claim 1 wherein said 2D vertical plane robot arm includes a 3D fast scanning stages group provided with said 2D vertical plane robot arm, said 3D fast scanning stages group performs detector raster scans.

7. The precision robot arm system as recited in claim 1 wherein said 2D vertical plane robot arm provides effective positioning and manipulating of said X-ray detector at an X-ray nanoprobe beamline.

8. The precision robot arm system as recited in claim 1 said 2D vertical plane robot arm provides a set load capacity with micron level positioning repeatability.

9. A precision robot arm system comprising:
    a two-dimensional (2D) vertical plane robot arm including duo-vertical-stages and a kinematic linkage system; said 2D vertical plane robot arm including a first high rigidity cross-roller bearing structure and a second high rigidity cross-roller bearing structure; and
    a robot arm vertical support carrying said 2D vertical plane robot arm; said vertical support including spaced apart rails respectively engaging said first high rigidity cross-roller bearing structure and said second high rigidity cross-roller bearing structure carried by the 2D vertical plane robot arm, such that said 2D vertical plane robot arm is rotatable and slidingly moved along said vertical support.

10. The precision robot arm system as recited in claim 9 further comprising a 2D horizontal base stage supporting said robot arm vertical support carrying said 2D vertical plane robot arm, said 2D horizontal base stage for precisely positioning said 2D vertical plane robot arm.

11. The precision robot arm system as recited in claim 9 further comprising a 3D fast scanning stages group provided with said 2D vertical plane robot arm for moving and precisely positioning said 2D vertical plane robot arm, said 3D fast scanning stages group performs detector raster scans.

12. The precision robot arm system as recited in claim 9 wherein said first bearing structure and said second bearing structure include a respective bearing formed of a stainless steel material.

13. The precision robot arm system as recited in claim 9 wherein said 2D vertical plane robot arm is formed of a selected material of aluminum, natural granite, synthetic granite, carbon fiber, and a combination of thereof.

14. The precision robot arm system as recited in claim 9 wherein said 2D vertical plane robot arm carries an X-ray detector providing effective positioning and manipulating of said X-ray detector at an X-ray nanoprobe beamline.

15. A method for implementing precision robot arm system comprising:
    providing a two-dimensional (2D) vertical plane robot arm including duo-vertical-stages and a kinematic linkage system;
    providing the 2D vertical plane robot arm with a first high rigidity cross-roller bearing structure and a second high rigidity cross-roller bearing structure; and
    providing a vertical support member carrying the 2D vertical plane robot arm; said vertical support including spaced apart rails respectively engaging said first high rigidity cross-roller bearing structure and said second high rigidity cross-roller bearing structure carried by the 2D vertical plane robot arm, such that said 2D vertical plane robot arm is rotatable and slidingly moved along said vertical support.

16. The method as recited in claim 15 wherein providing the 2D vertical plane robot arm includes providing a 2D horizontal base stage supporting said robot arm vertical support carrying said 2D vertical plane robot arm, said 2D horizontal base stage for precisely positioning said 2D vertical plane robot arm.

17. The method as recited in claim 15 wherein providing the 2D vertical plane robot arm includes providing a 3D fast scanning stages group with said 2D vertical plane robot arm for moving and precisely positioning said 2D vertical plane robot arm, said 3D fast scanning stages group performs detector raster scans.

* * * * *